United States Patent [19]

Moseman

[11] Patent Number: 4,668,419

[45] Date of Patent: May 26, 1987

[54] LIQUID FOOT TREATMENT COMPOSITION

[76] Inventor: Roger E. Moseman, 19400 Redwing Blvd., Hastings, Minn. 55033

[21] Appl. No.: 858,966

[22] Filed: May 2, 1986

Related U.S. Application Data

[63] Continuation-in-part of Ser. No. 682,656, Dec. 17, 1984, Pat. No. 4,589,994.

[51] Int. Cl.$^4$ .................. C11D 9/50; C11D 10/04
[52] U.S. Cl. .................. 252/107; 252/106; 252/110; 252/547; 252/DIG. 5; 252/DIG. 14; 514/731; 514/737; 424/196.1
[58] Field of Search ........ 252/107, 106, 547, DIG. 5, 252/DIG. 14; 514/196.1, 731, 737

[56] References Cited

U.S. PATENT DOCUMENTS

| | | | |
|---|---|---|---|
| 2,153,143 | 4/1939 | Figg, Jr. et al. | 87/5 |
| 2,251,934 | 8/1941 | Hartung | 252/107 |
| 2,698,301 | 12/1954 | Schumard | 252/107 |
| 2,906,664 | 9/1959 | Maurice | 167/31 |
| 3,063,895 | 11/1962 | Pearson et al. | 167/31 |
| 3,326,808 | 6/1967 | Noseworthy | 252/106 |
| 3,538,217 | 11/1970 | Dewar et al. | 424/173 |
| 3,703,472 | 11/1972 | Shaw et al. | 252/107 |
| 3,793,233 | 2/1974 | Rose et al. | 252/547 |
| 3,824,190 | 7/1974 | Winicov et al. | 252/106 |
| 3,943,234 | 3/1976 | Roggenkamp | 424/343 |
| 4,075,350 | 2/1978 | Michaels | 424/316 |
| 4,124,520 | 11/1978 | Schwalley et al. | 252/106 |
| 4,153,570 | 5/1979 | Hennemann et al. | 252/121 |
| 4,157,977 | 6/1979 | Dewar et al. | 252/106 |
| 4,225,471 | 9/1980 | Claus et al. | 252/547 |
| 4,371,461 | 2/1983 | Jones et al. | 252/547 |

FOREIGN PATENT DOCUMENTS

| | | |
|---|---|---|
| 245119 | 3/1959 | Australia . |
| 1153267 | 9/1983 | Canada . |
| 1040543 | 9/1966 | United Kingdom . |
| 1104692 | 2/1968 | United Kingdom . |
| 1311886 | 3/1973 | United Kingdom . |
| 1417117 | 12/1975 | United Kingdom . |
| 1464716 | 2/1977 | United Kingdom . |

*Primary Examiner*—Prince E. Willis
*Attorney, Agent, or Firm*—Merchant, Gould, Smith, Edell, Welter & Schmidt

[57] ABSTRACT

Aqueous concentrates and soaking solutions effective to clean and deodorize feet, and to protect them from fungal infections are disclosed. The compositions comprise a phenolic antifungal compound and a terpenic oil which are dissolved or dispersed in water by means of two foam-producing nonionic surfactants and a fatty acid salt.

15 Claims, No Drawings

LIQUID FOOT TREATMENT COMPOSITION

CROSS-REFERENCE TO RELATED APPLICATION

This application is a continuation-in-part of U.S. patent application Ser. No. 682,656, filed Dec. 17, 1984, now Pat. No. 4,589,994.

BACKGROUND OF THE INVENTION

A number of compositions designed to control foot odor, perspiration and the athlete's foot fungus are commercially available. Powdered foot treatment compositions commonly employ an absorptive material such as talc or silica, in combination with active ingredients such as fragrance, deodorants and anti-fungal agents. These compositions are designed to be sprinkled onto the feet or used to impregnate socks or shoe insoles. The active ingredients can also be delivered in organic solvents via aerosol spray systems. Although such formulations may deliver effective amounts of active ingredients to sweaty or irritated feet, they suffer from a number of disadvantages. In the first place, the drying action of the absorbent particles and aerosol sprays can roughen or harden the skin of the feet, while the use of organic carrier solvents can lead to irritation. In the second place, the solid compositions are not intended to clean the feet, but rather deposit of powder which can soil shoes and clothing. Finally, compositions designed for aerosol delivery pose the risk of user inhalation of volatile solvents such as methylene chloride.

Moseman (U.S. patent application Ser. No. 682,656, filed Dec. 17, 1984) discloses a foot treatment composition in the form of an aqueous concentrate which can be diluted with water to form a foot-soaking bath. The aqueous concentrate comprises a four-component anionic surfactant system, at least one foamable nonionic surfactant, a fragrant terpene-rich oil and an effective amount of a phenolic anti-fungal agent. Although the diluted concentrate is effective to clean and deodorize the feet, the concentrate is not satisfactory with respect to its phase stability, as it tends to curdle and separate upon standing.

Therefore, a need exists for a physically and/or chemically stable aqueous concentrate which can be diluted to yield a foot treatment composition which will both clean the feet and deliver effective amounts of fragrance and a fungistatic agent thereto. A further need exists for a composition having a high deodorant and fungistatic activity which does not soil or unduly dry the skin of the feet.

BRIEF DESCRIPTION OF THE INVENTION

The present invention is directed to a liquid foot treatment composition in the form of an aqueous concentrate which can be diluted with water to form a foot-soaking bath. The aqueous concentrate comprises a two-component foamable nonionic surfactant system, a fatty acid salt, a fragrant terpene-rich oil and an effective amount of a phenolic antifungal agent. When diluted and employed periodically as a foot-soaking bath, the present composition is effective to clean the feet and eliminate fungi and odor-causing bacteria without unduly depleting the natural skin oils.

Furthermore, the concentrate of the invention is phase-stable, and so can be stored for prolonged periods of time without coagulation or separation. Thus, the present concentrate is a marked improvement over the concentrates disclosed in Ser. No. 682,256, filed Dec. 17, 1984; the disclosure of which is incorporated by reference herein.

DETAILED DESCRIPTION OF THE INVENTION

The foot treatment compositions of the present invention are preferably formulated as liquid concentrates having an effective amount of a phenolic antifungal compound and a fragrance comprising a terpene-rich oil dispersed or dissolved in a major proportion of water with the aid of an nonionic-anionic surfactant system.

Antifungal Agent

The present concentrates will incorporate an amount of a phenolic compound effective to substantially reduce or eliminate the athlete's foot fungus and odor-causing bacteria. Useful phenolic biocides include phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butyl-phenol and o-benzyl-p-chlorophenol. The biologically-active, water soluble salts of these compounds may also be employed, e.g., the alkali metal salts. Of these compounds o-benzyl-p-chlorophenol is preferred due to its high biocidal power.

Terpene Oil

A fragrant, terpene-rich oil will be included in the present concentrates for cosmetic purposes. Preferred oils for use in the present concentrates include anise, cinnamon, clove, coriander, eucalyptus, fennel, lavender, lemon, orange, orange flower peppermint, pine, spearmint and compound bouquets thereof. Pine oils are preferred for use in the present formulations. Such oils are commonly prepared by solvent extraction or destructive distillation of pine, cedar or similar resinous woods, and can incorporate copaene, alpha-cedrene and longifolene as the major terpenic components.

Surfactant System

The phenolic biocide, terpene oil and other water-insoluble adjuvants will preferably be dispersed or solubilized in the aqueous base by means of a nonionic-anionic surfactant system, which also functions to enhance the cleaning power of the composition.

A. Nonionic Surfactant

The present foot treatment composition will include an amount of at least one member of two classes of nonionic surfactants, which can function to foam the present concentrates when they are diluted with warm water and which can aid in homogeneously dispersing the other constituents.

Preferred foamable nonionic detergents include the amine oxides, such as the $C_{10}$–$C_{20}$-alkyl-di(lower)alkyl-amine oxides, the $C_{10}$–$C_{20}$-alkyl-di(lower)hydroxyalkyl-amine oxides, or the [$C_{10}$–$C_{20}$-alkylamido($C_2$–$C_5$)alkyl]di(lower)alkyl-amine oxides, or mixtures thereof. Especially preferred members of this class include lauryl(dimethyl)amine oxide (Ninox ®L, Stephan Chem. Co., Northfield, Ill.), coco(dimethyl)amine oxide (Ninox ® C, Stephan Chem. Co., Northfield, Ill.), myristyl(dimethyl)amine oxide, stearyl(dimethyl)amine oxide (Schercamox ® DMS, Scher Chemicals, Inc., Clifton, N.J.), coco(bis-hydroxyethyl)amine oxide (Schercamox ® CMS), tallow(bis-hydroxyethyl)amine oxide and cocoamidopropyl(dimethyl)amine oxide(Schercamox ® C-AA).

The other useful class of nonionic surfactants are the hydroxypolyalkylenoxy(alkyl)benzene surfactants of the general formula: $C_6$–$C_{18}$-n-alkyl-phenyloxy$(EtO)_nH$ wherein n is about 3–20, preferably about 5–15. Other useful surfactants of this class are disclosed in Canadian Pat. No. 729,071, the disclosure of which is incorporated by reference herein. These nonoxynol surfactants are commercially available as the Igepal ® series from GAF Corp., e.g., Igepal ® CO-630 ($C_9$-alkyl, n=9) and Igepal CO-660 ($C_9$-alkyl, n=10).

B. Anionic Surfactant

The anionic surfactant component of the present composition will be selected from one or more of the common fatty acid salts or "soaps," including the water-soluble alkali-metal salts of $C_{10}$–$C_{18}$-saturated and unsaturated fatty acids and mixtures thereof. Commercially-available fatty acid salts useful as the soap component of the present compositions include sodium cocoate, sodium laurate, sodium palmitate, sodium tallowate, sodium stearate, sodium oleate, sodium linoleate, sodium linolenate and the like. The ethanolamine salts of $C_{10}$–$C_{18}$ saturated and unsaturated fatty acids are also useful as the soap component of the present composition. Commercially-available fatty acid salts of this class include the diethanol amine salts of linoleic acid and myristic acid and the triethanol amine salts of coconut fatty acid, myristic acid, oleic acid, palmitic acid and stearic acid.

Anionic surfactants such as the sulfate or sulfonate metal or ammonium salts disclosed in application Ser. No. 682,656 are not employed as components of the present compositions, as it is believed that they may contribute to the destabilization of the compositions disclosed therein.

Solvent System

The present foot treating concentrates will comprise a major proportion of water, preferably about 50–85%, most preferably about 55–80%, optionally in combination with minor amounts of a non-toxic lower alkanol cosolvent. The cosolvent can aid in the solubilization or dispersal of the phenolics, the oils, etc. Useful cosolvents will include about 0.5–10%, preferably about 1–5% of ethanol, isopropanol or mixtures thereof.

Adjuvants

The present compositions can also include an amount of glycerol effective to improve the emollient properties thereof, and can also include minor but effective amounts of other adjuvants including organic hardness ion sequestering agents such as tetrasodium EDTA, acidulent agents such as ammonium chloride, preservatives such as $C_1$–$C_4$ alkyl parabens, fragrance, dye and the like. When present, the adjuvants other than glycerol will individually be present at about 0.01–2% of the concentrate, preferably at about 0.1–1% of the concentrate.

Therefore, preferred cleaning, deodorizing and antifungal foot treatment concentrates will include, by weight, about 50–85% water, most preferably about 55–80% water; about 1–10%, most preferably about 2.5–7.5% of the amine oxide nonionic surfactant; about 1–10%, most preferably about 2.5–7.5% of the alkylphenol ethoxylate nonionic surfactant; about 2.5–15%, most preferably about 5–10% of an amine or an alkali metal salt of a fatty acid (a "soap"); about 0.1–10%, most preferably about 0.5–5% of a terpene rich oil, e.g., pine oil; about 0.1–10%, most preferably about 0.5–5% of a phenolic antifungal agent, e.g., o-benzyl-parachlorophenol, and optionally, about 1–10% glycerol and about 0.1–5% isopropanol.

Preferably, the amine oxide and the phenol ethoxylate are present in a weight ratio of about 1.5–0.75:1.0, most preferably about 1:1. Furthermore, the weight ratio of the total nonionic surfactants to the total anionic surfactants (the soap component) is preferably also about 1.5–0.75:1.0; most preferably about 1:1. It is believed that these proportions of nonionic surfactants and anionic surfactants contribute to the stability of the present concentrates.

In use the concentrates will typically be diluted with warm water to a concentration of about 0.3–5% and the resultant solution employed periodically to bathe or soak sweaty and/or dirty feet for an appropriate length of time, e.g., for 2–15 minutes. Feet thus treated are cleaned and remain deodorized and rendered resistant to infection by the athletes foot fungus for a period of at least one week.

The concentrates can be prepared by dissolving the water-conditioning agent, if any, in about 85–95% of the total water, followed by addition of any cosolvents, the surfactants, the terpenic oil, the phenolic agent and the glycerol, with appropriate agitation. The balance of the water is provided by the water present in the commercially-available surfactant formulations.

The invention will be further described by reference to the following detailed example.

EXAMPLE—FOOT TREATMENT CONCENTRATE

The constituents of Table I are blended in the weight percentages and in the order listed, to yield a homogeneous liquid foot treatment concentrate.

TABLE I

| Constituent | Weight Percent |
| --- | --- |
| Water | 59.3 |
| Igepal ® C0-630 (30% actives) | 16.5 |
| Ninox ® -L | 5.0 |
| Soap | 8.25 |
| Pine Oil | 2.5 |
| o-Benzyl-p-chlorophenol | 2.25 |
| Tetrasodium EDTA | 0.45 |
| Glycerol | 5.0 |
| Isopropanol | 0.75 |
| | 100.00% |

When diluted to 0.5 wt. % with warm tap water and employed periodically as a foot-soak bath, the concentrate is effective to clean and deodorize the user's feet and protect them from fungal infection, without unduly drying or irritating the skin. The present concentrate is also stable indefinitely when stored under ambient conditions in closed containers.

The invention has been described by reference to various specific and preferred embodiments and techniques. However, it should be understood that many variations and modifications may be made while remaining within the spirit and scope of the invention.

What is claimed is:

1. An aqueous concentrate effective to clean and deodorize feet consisting essentially of:
    (a) water;
    (b) about 1–10% of a $C_{10}C_{20}$-alkyl-di(lower)alkyl amine oxide, a $C_{10}$–$C_{20}$-alkyl-di(lower)hydroxyalkyl-amine oxide, a [$C_{10}$-$C_{20}$-alkylamido($C_2$-$C_5$)alkyl] di(lower)alkyl amine oxide or mixtures thereof;

(c) about 1-10% of a $C_6$-$C_{18}$-n-alkylphenyloxy(Eto)$_n$H, wherein n is about 3-20;

(d) about 2.5-15% of a fatty acid salt;

(e) about 0.1-10% of a phenolic antifungal agent; and (f) about 0.1-10% of a terpene-rich oil.

2. The aqueous concentrate of claim 1 wherein the weight ratio of component (b) to component (c) is about 1.5-0.75:1.

3. The aqueous concentrate of claim 1 wherein the weight ratio of components (b) and (c) to component (d) is about 1.5-0.75:1.

4. The aqueous concentrate of claim 1 which further includes about 1-10% glycerol.

5. The aqueous concentrate of claim 4 which further includes about 0.5-10% of a lower alkanol.

6. The aqueous concentrate of claim 1 wherein the terpene-rich oil includes pine oil.

7. The aqueous concentrate of claim 1 wherein the phenolic antifungal agent includes ortho-benzyl-parachlorophenol.

8. The aqueous concentrate effective to clean and deodorize feet consisting essentially of:

(a) about 55-80% water;

(b) about 2.5-7.5% of a $C_{10}$-$C_{20}$-alkyl-di(lower)alkyl amine oxide;

(c) about 2.5-7.5% of a $C_6$-$C_{18}$-n-alkyl-phenyloxy(EtO)$_n$H, wherein n is about 5-15;

(d) about 0.5-10% soap;

(e) about 0.5-5% pine oil;

(f) about 0.5-5% of a phenolic anti-fungal agent; and (g) about 1-10% glycerol.

9. The aqueous concentrate of claim 8 wherein the phenolic anti-fungal agent includes ortho-benzyl-parachlorophenol.

10. The aqueous concentrate of claim 8 wherein the amine oxide includes lauryl(dimethyl)amine oxide.

11. The aqueous concentrate of claim 8 wherein the weight ratio of component (b) and component (c) to component (d) is about 1:1.

12. A foot soaking or bathing solution formed by diluting the concentrate of claim 1 to about 0.3-5% with 13. A foot soaking or bathing solution formed by diluting the concentrate of claim 8 to about 0.3-5% with water.

14. A method of cleaning and deodorizing feet comprising periodically contacting them with the solution of claim 12.

15. A method of cleaning and deodorizing feet comprising periodically contacting them with the solution of claim 13.

* * * * *